United States Patent [19]

Laine et al.

[11] Patent Number: 4,788,309

[45] Date of Patent: * Nov. 29, 1988

[54] METHOD OF FORMING COMPOUNDS HAVING SI-N GROUPS AND RESULTING PRODUCTS

[75] Inventors: Richard M. Laine, Palo Alto; Yigal Blum, Menlo Park, both of Calif.

[73] Assignee: SRI International, Menlo Park, Calif.

[ * ] Notice: The portion of the term of this patent subsequent to Sep. 16, 2003 has been disclaimed.

[21] Appl. No.: 908,685

[22] PCT Filed: Mar. 4, 1986

[86] PCT No.: PCT/US86/00458

§ 371 Date: Mar. 4, 1986

§ 102(e) Date: Mar. 4, 1986

[87] PCT Pub. No.: WO86/06377

PCT Pub. Date: Nov. 6, 1986

Related U.S. Application Data

[63] Continuation-in-part of Ser. No. 727,415, Apr. 26, 1985, Pat. No. 4,612,383.

[51] Int. Cl.$^4$ .............................................. C07F 7/10
[52] U.S. Cl. .................................... 556/412; 556/410; 528/15; 528/28
[58] Field of Search ................... 556/412, 410; 528/28, 528/15

[56] References Cited

U.S. PATENT DOCUMENTS

| | | | |
|---|---|---|---|
| 2,564,674 | 8/1947 | Cheronis | 260/448.2 |
| 2,579,416 | 12/1951 | Cheronis | 260/2 |
| 2,579,417 | 12/1951 | Cheronis | 260/2 |
| 2,579,418 | 12/1951 | Cheronis | 260/2 |
| 2,968,530 | 1/1961 | Forgeng et al. | 23/203 |
| 3,007,886 | 11/1961 | Parker | 260/18 |
| 3,140,288 | 7/1964 | Peake | 260/288 |
| 3,393,218 | 7/1968 | Van Wazer | 260/448.2 |
| 3,518,289 | 6/1970 | Pearce et al. | 260/448.2 |
| 3,530,092 | 9/1970 | Borchert | 260/46.5 |
| 4,115,427 | 9/1978 | Kotzsch et al. | 260/448.2 |
| 4,255,549 | 4/1981 | Christophliemk et al. | 528/28 |
| 4,312,970 | 1/1982 | Gaul, Jr. | 526/279 |
| 4,340,619 | 7/1982 | Gaul | 477/228 |
| 4,395,460 | 7/1983 | Gaul | 428/408 |
| 4,397,828 | 8/1983 | Seyferth et al. | 423/344 |
| 4,404,153 | 9/1983 | Gaul, Jr. | 264/29.2 |
| 4,471,132 | 9/1984 | Hallgren | 556/410 |
| 4,482,669 | 11/1984 | Seyferth et al. | 524/442 |
| 4,482,689 | 11/1984 | Haluska | 528/25 |
| 4,535,007 | 8/1985 | Cannady | 422/226 |
| 4,540,803 | 9/1985 | Cannady | 556/412 |
| 4,543,344 | 9/1985 | Cannady | 501/92 |
| 4,612,383 | 9/1986 | Laine et al. | 556/412 |

OTHER PUBLICATIONS

Blum and Laine, *Organometallics* 5: 2081 (1986).
Fink, Walter, *Helv. Chim. Acta* 49:1408 (1966).
Kono and Ojima, *Organic Preparations and Procedures Int.* 5 (3): 135–139 (1973).
Kruger and Rochow, *J. Polymer Sc.* 2A: 3179:3189 (1964).
Legrow et al., "Ceramics from Hydridopolysilazane", *Mat. Res. Soc. Symp. Proc.* 73: 553–558 (Apr. 1986).
Sommer and Citron, *J. Org. Chem.* 32: 2470–2472 (1967).
Zoeckler and Laine, *J. Org. Chem.* 48:2539–2543 (1983).
Chem. Abs. 102: 224838s.

*Primary Examiner*—Paul F. Shaver
*Attorney, Agent, or Firm*—Ciotti & Murashige Irell & Manella

[57] ABSTRACT

Si-N groups in silazanes (which may be siloxazanes) are cleaved in the presence of a suitable catalyst or one or more reactants containing an Si-H group and an N-H group (in the same molecule or in different molecules) are reacted in the presence of a suitable catalyst. New silazane products result including oligomers and polymers. Suitable catalysts include metal carbonyl complexes and heterogeneous metal catalysts such as platinum on carbon. Immediate products of reaction such as products containing Si-H and N-H groups resulting from Si-N cleavage and Si-N products resulting from Si-H+N-H reactions undergo further reaction, resulting in many cases in a mixture of oligomers or of oligomers and polymers. The initial reactants may be open chain or ring compounds containing Si-N or Si-H+N-H in an open chain or in a ring or as pendant groups.

29 Claims, No Drawings

METHOD OF FORMING COMPOUNDS HAVING SI-N GROUPS AND RESULTING PRODUCTS

CROSS REFERENCE TO RELATED APPLICATION

This application is a continuation-in-part of copending United States application Ser. No. 06/727,415, filed Apr. 26, 1985, now U.S. Pat. No. 4,612,383, entitled "METHOD OF PRODUCING POLYSILAZANES."

BACKGROUND OF THE INVENTION

1. Field of the Invention

The invention relates to the synthesis of compounds (by which it is intended to include monomers, oligomers and polymers) containing the structure Si—N in the molecule. The invention concerns primarily silazanes which are useful to produce ceramic products on pyrolysis but it also relates to compounds which are siloxazanes and/or other compounds containing the Si—group.

2. Description of the Prior Art

Polysilazanes are useful among other things for the preparation of silicon nitride, $Si_3N_4$, by pyrolysis. Silicon nitride is a hard material and is useful in forming fibers for reinforcement of composite materials. See, for example, (a) Department of Defense Proceedings. Fourth Metal Matrix Composites Technical Conference, May 19-21, 1981, prepared for DOD Metal Matrix Composites Information Analysis Center and (b) J. J. Brennan, "Program to Study SiC Fiber-Reinforced Glass Matrix Composites, Annual Report to Dept. of Navy (November 1980), Contract No. N00014-78-C-0503.

A number of researchers have developed methods of forming polysilazanes, among them Redl and Rochow, who, in Angew. Chemie. (1964) 76, 650 discuss the preparation of polusilazanes by reaction (1)

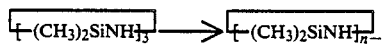
(1)

Brewer and Haber, J. Am. Chem. Soc. (1948) 70, 3888 and Osthoff and Kantor, Inorg. Syn. (1957) 5, 61 teach the reaction (2)

$(CH_3)_2SiCl_2 + NH_3 \rightarrow [(CH_3)_2SiNH]_n + HCl$ (2)

More recent work is described by Markle and others in R. A. Markle, I. Sekercioglu, D. L. Hill, R. R. Wills, and R. G. Sinclair, "Preparation of $Si_xN_yC_z$ Fibers by the Controlled Pyrolysis of Novel Organosilicon Polymeric Precursors", Final Report to NASA, Marshall Flight Center, Alabama, (1981), Contract No. NAS8-33223.

Zoeckler and Laine in J. Org. Chem. (1983) 48, 2539-2541 describe the catalytic activation of the Si—N bond and in particular the ring opening of octamethyl tetrasilazane,

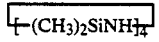

and polymerization of the ring-opened intermediate. Chain termination is effected by introducing $[(CH_3)_3Si]_2NH$ as a co-reactant giving rise to polymers $(CH_3)_3Si\text{-}[NHSi(CH_3)_2]_n\text{-}NHSi(CH_3)_3$ where n may be 1 to 12 or more depending upon the ratio of the chain terminator to the cyclic silazane. The catalyst used was $Ru_3(CO)_{12}$. Other publications are as follows: W. Fink, Helv. Chem. Acta., 49, 1408 (1966); Belgian Pat. No. 665774 (1965); Netherlands Pat. No. 6,507,996 (1965); D. Y. Zhinkis et. al., Rus. Chem. Rev., 49, 2814 (1980) and references 51-58; K. A. Andrianov et. al., Dok Akad. Nauk. SSSR, 227, 352 (1976); Dok Akad. Nauk. SSSR, 223, 347 (1975); L. H. Sommer et. al., JACS 91, 7061 (1969); L. H. Sommer, J. Org. Chem. (1967) 32 2470; L. H. Sommer et. al., JACS 89, 5797 (1967).

The methods described in the literature cited above and elsewhere have resulted in one or more of the following disadvantages: low yields of polysilazanes coincident with a high yield of cyclomers, lack of control over product selectivity or quality, etc. Often the product is volatile and is therefore difficult to pyrolyze if ceramic materials are desired from the solid or liquid polymer, or if it is solid, it is an intractable material which cannot be readily shaped, if indeed it can be shaped at all. The product is likely to be contaminated with halogen, especially chloride and it may be extensively cross linked and insoluble. In addition, the high ratio of Si to N in the polymers leads to formation of silicon along with $Si_3N_4$ on pyrolysis. In some instances excess carbon and SiC are also produced although they are not always desirable.

SUMMARY OF THE INVENTION

It is an object of the invention to provide improved methods of preparing compounds containing the Si—N group.

It is another object to provide methods of preparing compounds containing the Si—N group which permit selective control of the product.

Another object is to provide methods whereby the product of preparing compounds containing the Si—N group can be controlled during synthesis.

Another object is to provide methods whereby the product of preparing compounds containing the Si—N group can be modified after preparation.

Another object is to provide novel compounds containing the Si—group.

The above and other objects of the invention will be apparent from the ensuing description and the appended claims.

In accordance with the present invention a precursor containing an Si—group is caused to undergo cleavage of the Si—N bond or a compound containing the silyl group Si—H is reacted with an —NH group to produce hydrogen and one or more compounds containing an Si-N group.

Both types of reaction are carried out catalytically using a catalyst which is effective to activate the Si—N bond, the Si—H bond or the Si—Si bond.

Catalysts suitable for carrying out these reactions are metal complexes such as those in Table I which are homogeneous catalysts that dissolve in the reactants or in a solvent used to dissolve the reactants. Heterogeneous catalysts such as those in Table II may also be used. In general catalysts that activate the Si—H bond, the Si—N bond, or the Si—Si bond may be used.

The reactions are carried out in solution, the solvent being the reactants themselves or an added solvent. Suitable solvents are set forth in Table III. Temperature may range from −78° to 250° C., preferably 25° to 150°. (All temperatures are Celsius.)

Table 1, Homogeneous Catalysts $H_4Ru_4(CO)_{12}$, $Ru_3(CO)_{12}$, $Fe_3(CO)_{12}$, $Rh_6(CO)_{16}$, $Co_2(CO)_8$ $(Ph_3P)_2Rh(CO)H$, $H_2PtCl_6$, nickel cyclooctadiene, $Os_3(CO)_{12}$, $Ir_4(CO)_{12}$, $(Ph_3P)_2Ir(CO)H$, $Pd(OAc)_2$, $Cp_2TiCl_2$, $(Ph_3P)_3RhCl$, $H_2Os_3(CO)_{10}$, $Pd(Ph_3P)_4$, $Fe_3(CO)_{12}/Ru_3(CO)_{12}$ mixtures, also mixtures of metal hydrides.

Table 2, Heterogeneous Catalysts

Pt/C, Pt/BaSO$_4$, Cr, Pd/C, Co/C, Pt black, Co black Pd black, Ir/Al$_2$O$_3$, Pt/SiO$_2$, Rh/TiO$_2$, Rh/La$_2$O$_3$, Pd/Ag alloy, LaNi$_5$, PtO$_2$.

Table 3, Solvents

Ethers such as $Et_2O$, $CH_3O-CH_2CH_2OCH_3$, THF, halocarbons such as $CHCl_3$, $CH_2Cl_2$, $HClCF_2$, $ClCH_2CH_2Cl$, aromatics such as PhH, PhCH$_3$, Ph—OCH$_3$.

Where the reaction is of the second type (reaction of an Si—H group with an —NH group) the —NH group may be in the form of ammonia, a primary amine RNH$_2$, a secondary amine RRNH (the Rs being the same or different or forming part of a cyclic group), hydrazine, hydrazine derivatives. More generally the source of the —NH group may be described as

where the R's may be the same or different and may form part of a cyclic structure. R is commonly a hydrocarbon group, e.g. alkyl (e.g. methyl, ethyl, etc.), aryl (e.g. phenyl), cycloaliphatic (e.g. cyclohexyl) or aralkyl (e.g. benzyl) and the R's may be the same or different. R may also include an amino group, an alkoxy group, an ether group, an ester group, a silyl group, hydrogen, an alkenyl group, etc. The nitrogen of the —NH group may be present in various forms such as

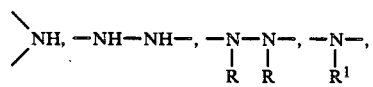

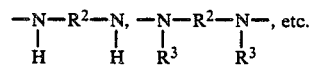

where $R^1$, $R^2$ and $R^3$ are defined as in R above, $R^2$ being, however, a bivalent group.

The following specific examples will serve to illustrate the practice and advantages of the invention.

EXAMPLE 1

Reaction of Diethylsilane with Ammonia

To 3.9 mmol (5 ml) of diethylsilane (Et$_2$SiH$_2$) are added 25 μmol of Ru$_3$(CO)$_{12}$ and the solution is heated at 135° C. under 60 psi of NH$_3$. The reaction is very fast producing oligomers, polymers and H$_2$. The H$_2$ pressure rises to 110 psi and is released every 0.5 hours. The reactor is again charged to 60 psi with NH$_3$. After 1 h all of the Et$_2$SiH$_2$ reacts and no further release of H$_2$ occurs.

EXAMPLE 1A

Reaction of Diethylsilane with Ammonia

To 20.0 mmol of diethylsilane (1.76 g) are added 25 μmol of Ru$_3$(CO)$_{12}$ (16 mg) and the solution is heated at 60° C. under approximately 80 psi of NH$_3$. After 1 hour, 85% of the silane is converted to a mixture of oligomers and the pressure increases by 200 psi due to H$_2$ evolution. Although Et$_2$SiH$_2$ disappears totally after 2 hours, chain oligomerization and cyclization continue for 12 hours. Oligomers of types A (n=3–5; major) B (n=1–4; major) C (n+n'=2 or 3), D (n+n'+n''+n'''=2) are found in the product mixture. Small quantities of other series —H[Et$_2$SiNH]$_n$H (n=2–4) and H$_2$N[Et$_2$SiNH]$_n$H (n=2) also appear in the solution

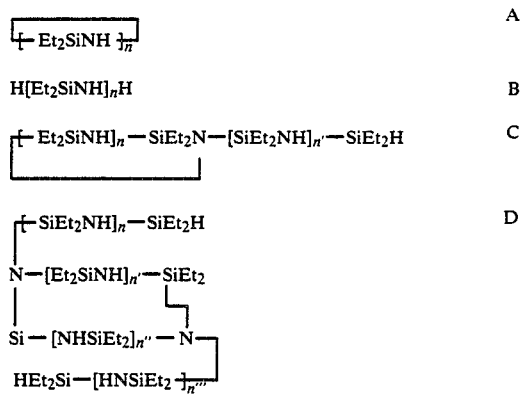

EXAMPLE 2

To 30 mmol of tetramethyldisilazane (TMDS) are added 25 μmol of Ru$_3$(CO)$_{12}$ and the solution is heated at 135° C. under 80 psi of NH$_3$. TMDS disappears totally after 20 h and polymerization continues for 28 h. The polymeric residue (heavy oil) is 2.44 gm (yield 61 wt%) after distillation at 180°/0.3 mm Hg with a Wt average MW of 764. The major polymeric series is the linear HSiMe$_2$[NHSiMe$_2$]$_x$NHSiMe$_2$H. Also smaller branched chain polymers appear. Molecular weights greater than 2000 can be obtained by varying the reaction conditions.

EXAMPLE 3

To 20 mmol of TMDS are added 25 μmol of Ru$_3$(CO)$_{12}$ and the solution is heated at 135° C. under 100 psi of NH$_3$. The conversion of TMDS is 94% after 1 h. 0.1 g of hydrazine are added and the solution is heated again for 3 hours. The GC shows that most of volatile products disappear. The high polymeric residue is 68 wt% after distillation at 180°/0.3 mm Hg. Similar results are achieved by using 200 mg of 5% Pt/C (activated under H$_2$) using identical conditions. The average molecular weight is 1200.

EXAMPLE 4

To 75 mmol of TMDS are added 25 μmol of Ru$_3$(CO)$_{12}$ and the solution is heated at 135° C. under 60 psi of ammonia. The hydrogen pressure produced in the reaction is released every 1 hour and the reactor is charged again with 60 psi of NH$_3$. TMDS disappears after 5 h. The initial turnover frequency (TF) for TMDS disappearance is 260. The net total turnover number for Si—N bond production is close to 4,480 after 8 hours.

EXAMPLE 5

To 20 mmol of tetramethyldisilazane (TMDS) and 20 mmol anhydrous hydrazine (NH$_2$NH$_2$) are added 25 μmol of Ru$_3$(CO)$_{12}$ and the solution is heated at 135° C. under nitrogen. All the TMDS disappears after 3 hours and H$_2$ pressure is obtained (TF=528). The yield of the polymeric residue after distillation of the volatile products is 75 wt percent. The average molecular weight is 968.

EXAMPLE 6

Reaction of n-Hexyl Silane with Ammonia 10.0 grams of n-hexyl silane

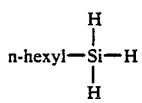

and 16 mg of Ru$_3$(CO)$_{12}$ as catalyst were heated at 60° C. under 150 psi of ammonia in a stainless steel reactor. A pressure of 300 psi is produced during the first hour. The reactor is cooled to room temperature, the pressure is released and the reactor is charged again with 150 psi of ammonia. This procedure is repeated several times. After 1 hour, 68% of the substrate disappears (according to calculations based on NMR analysis) and the reaction slows down. After 17 hours, only 12% of the starting material remains in the oily solution. Only a slight additional conversion is detected when the temperature is raised to 90° C. The addition of another 16 mg of Ru$_3$(CO)$_{12}$ promotes further conversion to a viscous material concurrently with the disappearance of hexylsilane. The N.M.R. and the VPO analyses are shown in Table 4.

TABLE 4

| Time (hours) | Form of Products | Conversion$^a$ (%) | Unit's Ratio$^b$ Si—H | N—H | Mn |
|---|---|---|---|---|---|
| 1$^c$ | light oil | 68 | 1.28 | 0.72 | — |
| 17$^c$ | slightly viscous | 88 | 1.18 | 2.18 | 921 |
| 24$^d$ | viscous oil | 91 | 1.06 | 2.20 | 962 |
| 28$^{d,e}$ | very viscous oil | 100 | 0.70 | 1.84 | 2772 |
| 36$^{d,e}$ | wax | 100 | 0.43 | 1.83 | 4053 |

$^a$Overall conversion was determined by NMR spectra in CDCl$_3$ (ppm). For n-hexylsilane: Si—H 3.52 (t, 3); C—H 1.36 (m, 8) and 0.92 (m, 5). For polysilazanes: Si—H 4.78 (m), 4.57 (m) and 4.36 (m); C—H 1.32 (m) and 0.91 (m); N—H 0.62 (m, br).
$^b$Si—H and N—H unit ratios are determined by NMR using the hexyl group integration as an internal standard.
$^c$At 60° C.
$^d$At 90° C.
$^e$After addition of 16 mg Ru$_3$(CO)$_{12}$.

The reaction mixture was analysed by NMR and GC-MS techniques to determine types of polymer. In Table 5 possible polymer types I, II, III, IV and V are set forth with elemental (C, H and N) analysis for each in the upper part of the table and actual analyses of the reaction mixture after 24 hours and 36 hours are set forth in the lower part of the table.

Certain conclusions may be drawn from Table 5, as follows:

a. The initial conversion is very fast; the initial turn-over frequency for silane conversion is 2350 per hour.

b. The polymer at 24 hours contains large quantities of Si—H bonds even when the molecular weights are high. Crosslinking, is therefore prevented, possibly as a result of steric hindrance.

c. At 36 hours the high integration ratio of N—H to C—H strongly suggests that there are significant quantities of the

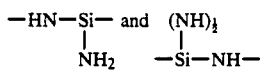

functional groups. Si—NH$_2$ can also be detected by I.R. (absorbance in 1550 cm$^{-1}$ in CCl$_4$). [(NH)$_\frac{1}{2}$ signifies that the NH group is shared with another fragment of the polymer.]

The GC-MS of the reaction solution shows a series of linear and cyclic oligomers with substituents on both the silicon, e.g., [(—N)$_3$Si—)] or nitrogen, e.g., [(—Si)$_3$N]. The terminal Si—NH$_2$ unit is not observed in the GC-MS fragmentation patterns.

Referring to Table 5, the types of repeating units of I through V are set forth below.

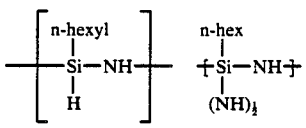

I        II

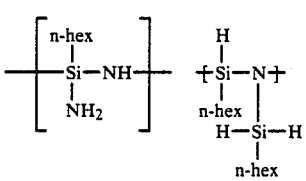

III        IV

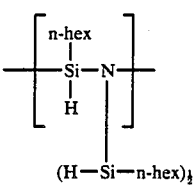

V

TABLE 5

| | Elemental Analysis | | |
|---|---|---|---|
| Type/hours | % C | % H | % N |
| I | 55.81 | 11.63 | 10.85 |
| II | 52.94 | 10.66 | 15.44 |
| III | 50.00 | 11.11 | 19.44 |
| IV | 59.25 | 11.93 | 5.76 |
| V | 58.37 | 11.35 | 7.57 |
| 28 h | 54.51 | 10.95 | 10.84 |
| 36 h | 52.54 | 10.73 | 12.93 |

The following conclusions are drawn from Table 5. The actual analyses at 28 hours conform closely to the linear type I polymer.

EXAMPLE 7

Reaction of Phenyl Silane ($C_6H_5SiH_3$) with Ammonia

Phenylsilane (10.0 g) and $Ru_3(CO)_{12}$ (16 mg) are heated at 60° C. under 150 psi of ammonia in a stainless steel reactor. The reactor is cooled several times during the reaction to sample and to recharge with ammonia. After 3 hours, 84% of the phenylsilane is converted to oligomers (calculated from NMR data). After 14 hours, the reaction temperature is increased to 90° C. and after 18 hours 8 mg $Ru_3(CO)_{12}$ are added to the mixture. Table 6 sums the observations and the results from the NMR and VPO analyses.

TABLE 6

| Time (hours) | Form of Products | Conversion (%) | Unit's Ratio Si—H | Unit's Ratio N—H | Mn |
|---|---|---|---|---|---|
| 3[c] | slightly viscous | 84 | 1.21 | 0.98 | 549 |
| 9[c] | slightly viscous | 95 | 1.13 | 1.32 | — |
| 14[c] | very viscous | 98 | 1.07 | 1.21 | 695 |
| 18[d] | hard wax | 100 | 0.98 | 1.03 | 1058 |
| 28[d,e] | solid | 100 | 0.47 | 1.47 | — |
| 32[d,e] | solid | 100 | 0.34 | 1.70 | 1432 |

[a-d]As in Table 4.
[e]Addition of 8 mg $Ru_3(CO)_{12}$ and 2 ml of toluene (removed before molecular weight measurements).

The data for the 18 hour sample indicate the formation of linear Type VI polymers (see Table 7). As additional catalyst is added and the temperature raised, more ammonia is incorporated in the polymer. After 32 h, the elemental and the NMR analyses indicate that the polymer contains units of types VI, VII, and VIII in the following approximate ratios:

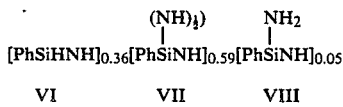

| | | |
|---|---|---|
| VI | VII | VIII |

The polymer containing units VI, VII and VIII is indicated as IX below.

This solid polymer IX after 32 hours is soluble in $CCl_4$, $CH_2Cl_2$, $CHCl_3$ and toluene. It has a glass transition point at 70°–72° C. and softens considerable at 90° C. Pyrolysis at 900° C. gives a 70% ceramic yield and finally 35% yield when heated to 1550° C. Only alpha and beta $Si_3N_4$ are observed by X-ray powder diffractometry although the final ceramic product contains 29% carbon (found by elemental analysis).

TABLE 7

| Type/hours | Elemental Analysis % C | % H | % N |
|---|---|---|---|
| VI | 59.50 | 5.78 | 11.57 |
| VII | 56.25 | 5.47 | 16.40 |
| VIII | 52.94 | 5.88 | 20.58 |
| 18 h | 59.37 | 5.67 | 11.81 |
| 32 h | 57.42 | 5.58 | 14.21 |
| IX | 57.25 | 5.60 | 14.97 |

GC-MS analysis of the mixture after 3 hours of heating reveals that majority of the oligomers (n=1–3) are type VI; minor products include cyclic compounds, cyclomers with branching on a silane unit and, straight and cyclic compounds branched on the nitrogen. Amine capped polymers are not observed.

EXAMPLE 8

Reaction of a Hydridosilazane $[H_2SiNMe]_x$ (2.0 g; Mn=560) and $Ru_3(CO)_{12}$ (16 mg) are heated under several reaction conditions. The results are shown in Table 8. The starting reactant —[$H_2SiNMe]_x$— is prepared from $H_2SiCl_2$ and $MeNH_2$ in ether solution as reported by Seyferth and Wiseman (Polymer Chem. Div. Preprints; Paper presented at the spring meeting of ACS, April 1984). The products are $[H_2SiNMe]_4$ and a linear oligomer $HNMe[SiH_2NMe]_x$—H (x is approximately 10).

TABLE 8

| Run | Gas Phase (atm) | Temp. (°C.) | Time (hours) | Form of Product | Ceramic Yields (%)[a] (Crystallized form) |
|---|---|---|---|---|---|
| 1 | $H_2$ (1 atm) | 60 | 4 | viscous liquid (Mn-1180; soluble in toluene and $CH_2Cl_2$) | 68 |
| 2 | $H_2$ (1 atm) | 135 | 2 | soft rubber | 75 |
| 3 | $MeNH_2$ (3 atm) | 60 | 4 | viscous liquid (Mn = 1200) | 78 ($\alpha Si_3N_4$)[b] |
| 4[c] | $NH_3$ (8 atm) | 60 | 2 | hard rubber | 85% ($Si_3N_4$; ($\alpha > \beta$) |

[a]Pyrolyzed under $N_2$ by ramping the temperature to 900° C. in 6 h and then holding for 2 h at 900° C.; sintered at 1550–1600° C.
[b]Poorly crystallized.
[c]Only 8 mg of $Ru_3(CO)_{12}$ were used.

EXAMPLE 9

Polymerization of Ethylsilane with Ammonia

Ethylsilane, ($EtSiH_3$, 8 g) is condensed into a stainless steel reactor, containing $Ru_3(CO)_{12}$ (16 mg) in 1 ml of toluene, cooled in a dry ice/acetone container. The reactor is then pressurized with 100 psi of ammonia (at −78° C.). A total pressure of 250 psi is obtained when the reactor is heated to room temperature. The solution is heated at 60°. The reactor is cooled after 1 hour to room temperature, depressurized (releasing $H_2$), loaded with an additional 150 psi of ammonia and reheated at 60° for an hour then cycled again for 2 hours. The resulting solution (after 4 h) is very viscous. The solvent is evacuated (R.T., 0.1 mm) and the waxy polymer is heated again at 90° for another 2 hours to form a soft rubber. Pyrolysis of the rubber at between 200° and 900° C. gives 58% of ceramic material. The NMR and IR spectra of the polymer produced after 4 hours show the following peaks: NMR (8, $CDCl_3$): Si—H (4.90–4.40, m); $CH_3$ (0.95, t); N—H (1.0–0.8 br); $CH_2$ (0.58, q). (The ratio of the Si—H to the Et—Si and N—H absorbance is 1:24 which suggests that the polymer consists of approximately 30% [EtSiHNH] units and the rest are [Et($NH_2$)SiNH] and [Et(NH)$_{0.5}$SiNH].
I.R. (cm$^{-1}$, $CH_2Cl_2$), Si—NH—Si (3385, 1170, 950); Si—$NH_2$ (1545); Si—H (2108); Si—Et [1235, 1012).

EXAMPLE 10

Polysiloxazane 1,1,3,3 tetramethyldisiloxane (5.36 g, 40 mmol ($HMe_2Si)_2O$) and $Ru_3(CO)_{12}$ (32 mg, 50 μmmol) are heated at 60° C. under $NH_3$ (150 psi). The pressure produced in the reactor is released and the reactor is recharged with $NH_3$ several times. 80% of the disiloxane is converted after 1.5 hours. The reaction is heated continuously for 20 hours.

GC-MS analysis indicates the following pattern:

A = —[Me$_2$SiOMe$_2$SiNH]$_n$— (n = 2-5)
B = H—[Me$_2$SiOMe$_2$SiNH]$_n$SiMe$_2$OSiMe$_2$H
  (n = 1-6)

A 70% yield is obtained after high vacuum distillation (180° C./0.5 mm). A$_2$ is isolated as solid (white crystals, mp. 37°, a single NMR absorption at 0.12 ppm. The residue is a viscous oil with Mn=5690 daltons.

| | Elemental analysis: | | | | |
|---|---|---|---|---|---|
| | % C | % H | % N | S | O |
| Polymer B | 32.65 | 8.84 | 9.52 | 38.10 | 10.88 |
| Found | 32.67 | 9.10 | 8.56 | 41.89 | 7.02 |

This is an example of preparing a polysiloxazane

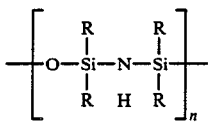

and these polysiloxazanes are believed to be novel compositions of matter. R may be hydrogen or an organic group (defined as above following Table 3). The nitrogen may be substituted, e.g. by an organic group R. The subscript n may have various values.

EXAMPLE 11

Reaction of Octamethylcyclotetrasilazane

Octamethylcyclotetrasilazane, referred to as 1, was reacted under various conditions with (+) and without (−) [(CH$_3$)$_3$Si]$_2$NH and with various catalysts. Results are set forth in Table 9.

TABLE 9
YIELD OF OLIGOMERS AND POLYMERS

| | | | | Yield (% Weight)$^c$ | | |
|---|---|---|---|---|---|---|
| Run$^a$ | Catalyst | [(CH$_3$)$_3$Si]$_2$NH | II Conv. (%)$^b$ | Oligomers | Polymers | M.W. |
| 1 | H$_2$SO$_4$ | − | 46 | 33 | 10 | 783 |
| 2 | H$_2$SO$_4$ | + | 46 | 18 | 33 | 587 |
| 3 | Ru$_3$(CO)$_{12}$/H$_2$ | − | 74 | 54 | 18 | 2551 |
| 4 | Ru$_3$(CO)$_{12}$/H$_2$ | + | 68 | 28 | 44 | 697 |
| 5 | Pt/C | − | 62 | 22 | 34 | 1080 |
| 6 | Pt/C | + | 71 | 28 | 45 | 784 |

$^a$The same conditions as shown in Table 10. The reactions were carried without internal standard and the analyses were made according to the distillation of the solutions.
$^b$The conversion measurement is due to the amount of 1 in the end of the reaction.
$^c$Yield is in weight percentage due to the total weight of the solution. The oligomer fraction also contains the disilazane (Me$_3$Si)$_2$NH which remains.

In the Ru$_3$(CO)$_{12}$ and H$_2$SO$_4$ catalysis the conversion of 1 was higher in the absence of [(CH$_3$)$_3$Si]$_2$NH although, in all three catalytic methods, the total weight of polymers obtained is greater when [(CH$_3$)$_3$Si]$_2$NH is added. One must consider the fact that the catalyst also attacks the disilazane Si—N bonds, so the total turnover number for breaking these bonds is greater when [(CH$_3$)$_3$Si]$_2$NH is used.

The average molecular weight analyses show that in spite of the higher yield of polymers there is a decrease in the molecular weight when the capping agent is used. This process can be improved by using higher ratios of 1 to [(CH$_3$)$_3$Si]$_2$NH.

The above results strongly suggest that the catalytic reaction approaches an equilibrium. When the reaction, catalyzed by H$_2$SO$_4$, is run until an equilibrium is achieved and then another equivalent of acid is added, no further reaction is observed.

The volatile oligomers fractions isolated by distillation, when reacted again with the catalyst, produced additional amounts of polymers. The same series of reactions shown in Table 9 are run with hexamethylcyclotrisilazane (2) instead of 1 as the starting material. All of them are reactive, producing the same oligomers and polymers, including 1. That is to say, an equilibrium results and selective separation of products from the equilibrium mixture can be carried out. For example the 1⇌2 equilibrium mixture may be distilled, thereby removing the lower boiling components including 2 and driving the reaction to the right.

GC-MS Analysis

Identification of polymer types produced in the reactions described in Table 9, were performed by GC-MS. This method is limited to polymers with molecular weights less than 1000. We have observed types A and B in reaction (1). B is the major product in run 4 (n=1-8) and A

[—Me$_2$SiNH—]$_n$      A

Me$_3$SiNH[Me$_2$SiNH]$_n$—SiMe$_3$      B appears in small quantities (n=3-7). Another set of polymers observed in even smaller quantities are C (n+n'=2.7) and D (n+n'+n"+n'''=2-6). C and D are crosslinked through nitrogen groups.

—[SiNH]$_n$—SiN—[SiNH]$_{n'}$—Si≡      C

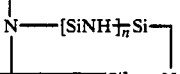
     D

In the above, Si signifies —SiMe$_2$— and Si≡ signifies —SiMe$_3$. In run 3 because of the high molecular weight no significant products could be detected by the GC-MS. Most likely there are more crosslinks from this run which also explains the high molecular weight. Run 6 shows the same types as the parallel reaction with Ru$_3$(CO)$_{12}$ but the quantities of C and D are larger. The Pt/C catalysis without the capping agent gives series A and other quantitive series E, F that indicate bi- and tri-cyclo crosslinked compounds.

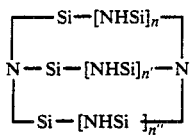

F contains another ring. In E, $n_{total}$ (i.e. $n+n'+n'')=5-8$; in F, $n_{total}=8-9$.

The polymers produced by $H_2SO_4$ catalysis contains types A (n=5, 6), B (n=2-8; major products), and C(n=2-5) in run 2 and A (n=5-9) in run 4. In both cases the GC-MS analyses show an amount of oxygenated products in which oxygen replaced amine groups.

EXAMPLE 12

To 1.8 gr polydimethylsilylhydrazine $[Me_2SiNHNH]_x$ prepared as follows:

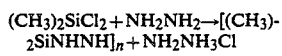

(average MW 1130) dissolved in 5 ml of toluene are added 25 μmol of $Ru_3(CO)_{12}$ and the solution is heated at 135° C. under hydrogen. The clear solution turns cloudy and viscous (at room temperature). 1.3 g of a soft solid product is obtained after distillation of the volatile products and solvent at 180°/0.3 mm Hg. The solid has a Wt average MW 1220 and starts to soften at 60° C. The same treatment for the starting material in the absence of catalyst gives a slightly cloudy solution at room temperature (clear during heating). The Wt average MW decreases to 612. The product is a solid after distillation and does not soften up to 250° C.

EXAMPLE 13

Octamethylcyclotetrasilazane 1 is reacted with $[(CH_3)_3Si]_2NH$ in the presence of various catalysts. The reaction conditions, catalysts and results are set forth in Table 10.

atmosphere pressure. The time figures indicate the shortest time in which there was no further conversion of 1. Butyl ether was used as an internal standard for gas chromatographic analysis. In the decomposition of catalyst column, "s" means slow, "m" means moderate and "f" means fast. In Run No. 4 the ratio of $Ru_3(CO)_{12}$ to $H_2O$ was 1:22. In Run No. 18, 200 mg of 5% Pt/C are used and in Run No. 20, 150 mg of 5% Pd/C are used with 4.15 grams of 1.

It will be seen that in the presence of hydrogen (Runs No. 3, 8, 11, 14 and 17) the reaction was much faster and gave significantly higher yields than in comparable runs with nitrogen. The mixed catayst in Run No. 6 resulted in a fast reaction and a high yield even in the absence of hydrogen. In Run No. 12 a nitrogen atmosphere is used. The reaction rate and yield are comparable to Run No. 11 where a hydrogen atmosphere is used, because of the presence of hydrogen in the complex. In Runs Nos. 7, 9 and 15 no appreciable reaction occurred.

EXAMPLE 14

Reaction of Hexamethylcyclotrisilazane with Ammonia and Hydrogen

A reactor loaded with hexamethylcyclotrisilazane, 2, (4.4 g) and $Ru_3(CO)_{12}$ (16 mg) is pressurized with $NH_3$ (150 psi) and $H_2$ (150 psi), then heated at 135° C. for 18 hours. The cyclotrimer is converted in 84% yield to form two major series of products-cyclomers (A; n=4-13) and branched cyclomers (B; n=1-6) analyzed by GC-MS.

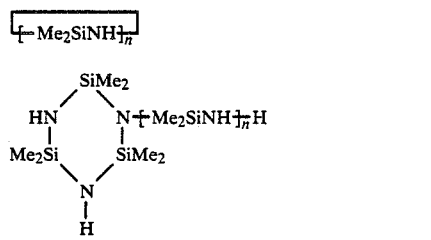

TABLE 10

| Run | Catalyst | Temp (°C.) | Time (h) | Conversion (%) | Decomposition of Catalyst |
|---|---|---|---|---|---|
| 1 | $Ru_3(CO)_{12}$ | 135 | 6 | 22 | s |
| 2 | $Ru_3(CO)_{12}$ | 180 | 15 | 80 | m |
| 3 | $Ru_3(CO)_{12}/H_2$ | 135 | 1 | 78 | — |
| 4 | $Ru_3(CO)_{12}/H_2O$ | 135 | 3 | 33 | s |
| 5 | $Ru_3(CO)_{12}/Fe(CO)_5$ | 135 | 6 | 26 | s |
| 6 | $Ru_3(CO)_{12}/Fe_3(CO)_{12}$ | 135 | 3 | 80 | s |
| 7 | $Fe_3(CO)_{12}$ | 135 | — | — | — |
| 8 | $Fe_3(CO)_{12}H_2$ | 135 | 3 | 80 | f |
| 9 | $Os_3(CO)_{12}$ | 135 | — | — | — |
| 10 | $Os_3(CO)_{12}$ | 180 | 20 | 78 | — |
| 11 | $Os_3(CO)_{12}/H_2$ | 135 | 6 | 73 | — |
| 12 | $H_2Os_3(CO)_{10}$ | 135 | 3 | 78 | — |
| 13 | $Rh_6(CO)_{16}$ | 135 | 20 | 55 | g |
| 14 | $Rh_6(CO)_{16}/H_2$ | 135 | 3 | 78 | g |
| 15 | $Ir_4(CO)_{12}$ | 135 | — | — | — |
| 16 | $Ir_4(CO)_{12}$ | 180 | 15 | 70 | m |
| 17 | $Ir_4(CO)_{12}/H_2$ | 135 | 3 | 76 | f |
| 18 | Pt/C | 135 | 3 | 75 | — |
| 19 | $PtO_2$ | 180 | 15 | 25 | — |
| 20 | Pd/C | 135 | 3 | 78 | — |

Comments on Table 10 are as follows: The molar ratio of 9, the silazane $[(CH_3)_3Si]_2NH$ and catalyst was 250:84:1. The reaction was carried out under hydrogen where indicated, as in Run No. 3, or water in Run No. 4, otherwise under nitrogen. The hydrogen was at 1

EXAMPLE 15

Copolymerization of Phenylsilane and 1,1,3,3,-tetramethyldisilazane

To a mixture of phenylsilane (4.32 g, 40 mmol) and 1,1,3,3,tetramethyldisilazane (5.32 g, 40 mmol) is added $Ru_3(CO)_{12}$ (16 mg, 25 μmol). The solution is heated at 60° under 150 psi of ammonia. After 5 h, the GC shows high boiling products and the loss of 95% of the starting materials. After 8 hours the reaction temperature is increased to 90° C. and after another 2 hours to 135° C. The reaction run for 30 hours. The final results is a viscous oil consisting of a mixture of products. Very little comes off the gc at this point which indicates high molecular weight products. Evaporation of the remaining volatile products (230°/2 mm) leaves a waxy residue. IR, NMR and GC/MS of this product are taken to examine the copolymerization between the two starting substrates. An Si—H bond appears clearly in the IR spectrum but it cannot be observed in the NMR spectrum which is analytically less sensitive. The elemental analysis and the NMR integration suggest that the copolymer contains the following average structure.

| [PhSiHNH]$_{1.3}$[Me$_2$SiNH]$_2$ | | | | X |
|---|---|---|---|---|
| Elemental analysis: | C | H | N | Si |
| Calculated for X: | 46.69 | 7.61 | 15.23 | 30.44 |
| Found: | 46.45 | 7.05 | 15.91 | 30.88 |

EXAMPLE 16

Reaction Between Hexamethylcyclotrisilazane and Diethylsilane 15 mg (25 μmol) of $Ru_3(CO)_{12}$ are added to 2.19 g (10 mmol) of hexamethylcyclotrisilane (—[Me$_2$SiNH]$_3$—) and 0.88 g (10 mmol) of diethylsilane (Et$_2$SiH$_2$) and the solution is heated at 135° C. for 20 h. N-diethylsilane-hexamethylcyclotrisilazane

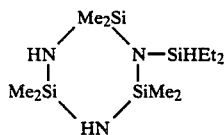

is the major product (3.7 mmol) identified by GG-MS and NMR. Other minor products are (HEt$_2$Si)$_2$NH and N-dimethylsilane-hexamethylcyclotrisilazane. A residue of 28% yield remains after evaporation at 180° C. (0.5 mm). The N-diethylsilyl-cyclotrisilazane is isolated by distillation and identified by GC-MS and NMR.

EXAMPLE 17

Reaction of 1,2,3,4,5,6 Hexamethylcyclotrisilazane with Ammonia

To 4.39 gr of

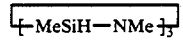

are added 16 mg of $Ru_3(CO)_{12}$ and the solution is heated under 150 psi of ammonia at 60° C. The reactant disappears after 5 hours. The reactor is again charged with ammonia and heated again at 90° for 33 hours. The product is a viscous oil having Mn=691 which gives 57% yield of ceramic material. GC-MS analysis of the oligomeric fraction indicates the substitution of Si—H groups by Si—NH groups together the substitution of N—Me groups by N—H in the cyclomeric structure.

EXAMPLE 18

Polymerization of Tetramethyldisilazane in the Presence of Ammonia (a) To 100.0 mmol of TMDS (13.3 g) are added 50.0 μmol of $Ru_3(CO)_{12}$ (32.0 mg) and the solution is heated under ammonia under various reaction conditions as noted in Table 11. The volatile oligomers were separated from the solution by vacuum distillation (up to 180°/300μ). The residue is the nonvolatile fraction.

Our initial evaluation of this reaction, using either the homogeneous ruthenium catalyst or activated Pt/C gives cyclomers (n=3–7), linear oligomers, n=2–11), and very small amounts of branched oligomers, (n=1–7<5%) as evidenced by the GC-MS analyses.

TABLE 11

THE EFFECTS OF TEMPERATURE AND AMMONIA PRESSURE ON PRODUCT SELECTIVITY IN THE REACTION TMDS WITH NH$_3$ IN THE PRESENCE OF Ru$_3$(CO)$_{12}$

| Run | NH | Temp. (°C.) | Time$^a$ (Hours) | Turnover$^b$ Frequency | | Yield of Cyclomers in the volatile fraction (%) | | Nonvolatile Oligomer Yield (%) | Ave. M.W. (Mn) |
|---|---|---|---|---|---|---|---|---|---|
| | | | | TMDS Conversion | Si—H Disappearance | Total | Tricyclomer | | |
| 1 | 1 | 60 | 66 | 640 | 1000 | 39 | 25 | 19 | 1297 |
| 2 | 1 | 90 | 60 | 720 | 1160 | 34 | 18 | 21 | 1006 |
| 3 | 13 | 60 | 12 | 1220 | 1300 | 88 | 69 | 19 | 2024 |
| 4 | 13 | 90 | 8 | 1960 | 3438 | 91 | 70 | 5 | 1425 |

$^a$At these reaction times, the catalyst is still active but the rate of reaction is considerably reduced because of the low Si—H bond concentration.
$^b$TF (mol substate/mol cat/h) based on initial rates, determined by GC (TMDS conversion) and NMR integration (Si—H signal disappearance) referenced to the CH$_3$—Si signals.

GENERAL DISCUSSION

It will be apparent that two general types of reaction occur. In type (a) (cleavage of an Si—N bond, illustrated by Examples 11–14) a ring is opened at an Si—N group to separate the silicon and nitrogen (or an open chain is cleaved at an Si—N group) and the resulting fragment or fragments react with one another and/or with a reactant such as ammonia, an amine, hydrogen, etc. The immediate reaction products will undergo further reaction, which may comprise the second type of reaction (see below).

In type (b) reaction (reaction of Si—H with a nitrogen compound HNRR) a compound Si—NRR results as the immediate product and will undergo further reaction with SiH or with the products of reaction or with an added reactant. The R's, which may be the same or different and which may be parts of a cyclic structure, are as defined above.

In the type (b) reaction the Si—H reactant may be silane itself, SiH$_4$. Also in the type (b) reaction where the silazane

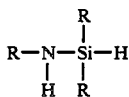

is reacted with H$_2$NR the disilazane

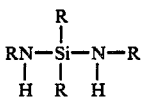

which is a new compound, results (R defined as above). Where TMDS is reacted with ammonia the resulting product is

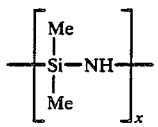

where x is greater than unity. The product is a mixture.

It will be apparent that cleavage of an Si—N group or reaction of Si—H with H—N usually leads to successive reactions which may be cleavage [type (a)] or Si—H+H—N [type (b)] reactions or a mix of both types of reactions. It should also be noted that Si—Si bonds are cleaved under many of the reaction conditions described above resulting in Si—H groups which undergo reaction with H—N groups.

It will therefore be apparent that new and useful methods of preparing oligomers and polymers having Si—N groups have been provided as have new and useful compositions of matter.

We claim:

1. A method of producing a silazane containing at least two Si—N groups which comprises
   (a) providing a precursor containing at least one Si—N group, catalytically cleaving an Si—N bond in the presence of a metal catalyst capable of activating Si—N bonds, such cleavage being carried out in the presence of hydrogen or a hydrogen donor, and reacting the cleavage product to produce the desired silazane, or
   (b) providing one or more reactants which provide an Si—H group and an —NH group and causing reaction to occur between Si—H and —NH groups in the presence of a catalyst capable of activating Si—H and Si—N groups, such reaction resulting in formation of an Si—N group.

2. The method of claim 1 wherein the reaction is conducted under conditions to cause the initial product or products to undergo further reaction to provide other products.

3. The method of claim 2 wherein the reaction products are controllable by the choice and/or amount of catalyst.

4. The method of claim 2 wherein the reaction products are controllable by choice of temperature.

5. The method of claim 2 wherein the reaction products are controllable by the choice of solvent.

6. The method of claim 1 wherein the initial reaction product or products are the result of reaction of type (a) or of type (b) and further reaction of type (b) or type (a) is caused to ensue.

7. The method of claim 2 wherein the reaction is caused to proceed to the point of producing oligomeric or polymeric polysilazanes which are viscous liquids or solids at room temperature.

8. The method of claim 1 wherein the reaction is initially of type (a).

9. The method of claim 8 wherein the precursor is a cyclic silazane and the initial reaction product is a cleavage product resulting from cleavage of an Si—N group in the ring.

10. The method of claim 9 wherein further reaction of the initial product or products is caused to take place and such further reaction may be of type (a) or type (b) or both.

11. The method of claim 8 wherein the precursor is a linear silazane and the initial reaction product is a cleavage product resulting from cleavage of an Si—N group in the linear silazane.

12. The method of claim 11 wherein further reaction of the initial product or products is caused to take place and such further reaction may be of type (a) or type (b) or both.

13. The method of claim 1 wherein the reaction is initially of type (b).

14. The method of claim 13 wherein the Si—H group and the N—H group are present in different compounds.

15. The method of claim 13 wherein the Si—H and N—H groups are present in the same compound.

16. The method of claim 14 or claim 15 wherein further reaction of the initial product or products is caused to take place and such further reaction may be of type (a) or type (b) or both.

17. A method of preparing polysilazanes having the repeating structure I $$-Si-N- \qquad \qquad I$$

which comprises:
(a) providing a starting material having the structure II in its molecule $$-Si-A \qquad \qquad II$$

in which A is hydrogen, N< or Si—, structure II being part of a linear structure or part of a cyclic structure
(b) providing a catalyst which is effective to activate Si—H, Si—N and/or Si—Si bonds, and
(c) reacting the starting material in the presence of such catalyst with (1) hydrogen where A is nitrogen and structure II is part of a cyclic silazane or (2) with H—X—H in other cases, X being selected from the group

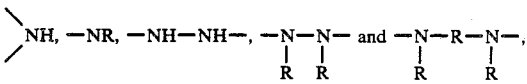

R being hydrogen or an organic group or a silyl group
(d) thereby forming a polymer having the repeating unit —Si—N—

18. The method of claim 17 wherein R is hydrogen or a hydrocarbon group.

19. The method of claim 17 wherein the catalyst is a homogeneous catalyst.

20. The method of claim 19 wherein the catalyst is a metal complex.

21. The method of claim 20 wherein the catalyst is a metal carbonyl cluster.

22. The method of claim 17 wherein the catalyst is a heterogeneous catalyst.

23. The method of claim 17 wherein the reaction is carried out in an organic solvent at a temperature of about 78° to 250° C.

24. The method of claim 17 wherein the starting material is a linear or cyclic silazane and it is reacted with hydrogen.

25. The method of claim 17 wherein the starting material is a linear or cyclic silazane and it is reacted with H—X—H.

26. The method of claim 25 wherein H—X—H is ammonia.

27. The method of claim 25 wherein H—X—H is a primary amine.

28. The method of claim 25 wherein H—X—H is hydrazine or a substituted hydrazine.

29. The method of claim 17 wherein the starting material is a cyclic compound containing an Si—Si bond in the ring and it is reacted with H—X—H.

* * * * *

UNITED STATES PATENT AND TRADEMARK OFFICE
CERTIFICATE OF CORRECTION

PATENT NO. : 4,788,309

DATED : November 29, 1988

INVENTOR(S) : Richard M. Laine and Yigal Blum

It is certified that error appears in the above-identified patent and that said Letters Patent is hereby corrected as shown below:

At Column 1, Line 12, between the title of the invention and the section entitled "Cross Reference To Related Application" insert the following:

"This invention was funded in part by the Office of Naval Research under Contract No. N00014-84-C-0392."

Signed and Sealed this

Ninth Day of May, 1995

*Attest:*

BRUCE LEHMAN

*Attesting Officer*      *Commissioner of Patents and Trademarks*